(12) United States Patent
Nüesch

(10) Patent No.: US 6,270,474 B1
(45) Date of Patent: Aug. 7, 2001

(54) BREAST PUMP AND BREAST PUMP VALVE

(75) Inventor: Heinrich Nüesch, Zuzwil (CH)

(73) Assignee: Nuesch Logistik, Zuzwil (CH)

( * ) Notice: Subject to any disclaimer, the term of this patent is extended or adjusted under 35 U.S.C. 154(b) by 0 days.

(21) Appl. No.: 09/331,051

(22) PCT Filed: Dec. 10, 1997

(86) PCT No.: PCT/CH97/00460

§ 371 Date: Jun. 16, 1999

§ 102(e) Date: Jun. 16, 1999

(87) PCT Pub. No.: WO98/26817

PCT Pub. Date: Jun. 25, 1998

(30) Foreign Application Priority Data

Dec. 16, 1996 (DE) .............................. 196 52 232

(51) Int. Cl.[7] ................................... A61M 1/06
(52) U.S. Cl. ..................... 604/74; 604/313; 604/346
(58) Field of Search .............................. 604/73–76, 313, 604/315, 346, 320, 119

(56) References Cited

U.S. PATENT DOCUMENTS

| | | |
|---|---|---|
| 4,673,388 | 6/1987 | Schlensog et al. . |
| 4,799,922 * | 1/1989 | Beer et al. ............... 604/74 |
| 4,857,051 * | 8/1989 | Larsson ................... 604/74 |
| 4,886,494 | 12/1989 | Morifuji . |
| 4,929,229 | 5/1990 | Larsson . |
| 5,071,403 * | 12/1991 | Larsson ................... 604/74 |

FOREIGN PATENT DOCUMENTS

| | | |
|---|---|---|
| 0 198651 * | 10/1986 | (EP) . |
| 0 198 651 | 10/1986 | (EP) . |
| 2 673 260 | 8/1992 | (FR) . |
| WO 96/24791 | 8/1996 | (WO) . |

* cited by examiner

Primary Examiner—Anhtuan T. Nguyen
Assistant Examiner—Jeremy Thissell
(74) Attorney, Agent, or Firm—Burns Doane Swecker & Mathis L.L.P.

(57) ABSTRACT

A breast pump fitted with an element to be applied on a woman's breast, including an outflow duct and a pumping device branching off from the outflow duct through a first bypass. Another bypass leads to a milk collector through a check valve, which is fitted with a valve body with at least one outlet for the milk pumped on the front face and a valve reed of flexible material, intended to seal the outlet during suction, and which is connected to the valve body through a connecting device having on the edge of its front face a hinge for a valve reed freely extending from the hinge over at least part of the front face. In an another embodiment, the bypass in which the valve is located may be oriented downwards relative to the outflow duct, and the bypass in which the pumping device is located, or at least some segments of it, may be oriented upwards. To control the suction effect on the breast, an infiltrated air inlet can be provided in one of the ducts an/or bypasses or in a pipe connected thereto.

5 Claims, 2 Drawing Sheets

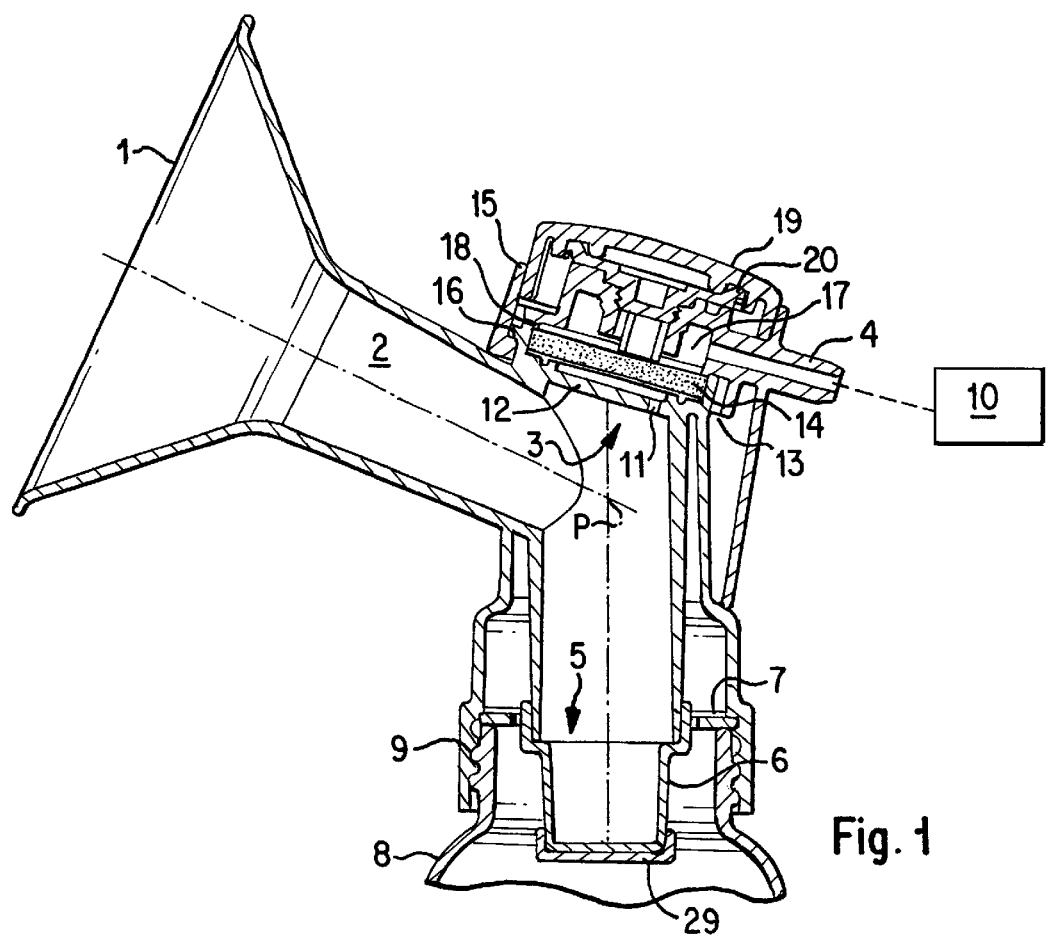
Fig. 1
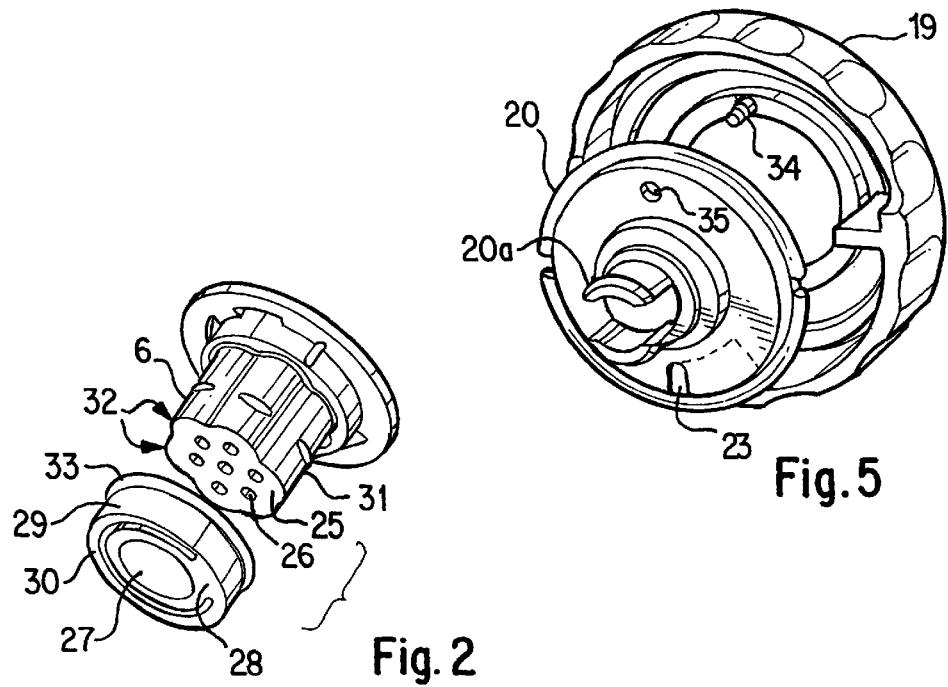
Fig. 2
Fig. 5

BREAST PUMP AND BREAST PUMP VALVE

BACKGROUND OF THE INVENTION

The invention relates to a breast pump.

Breast pumps comprising a non-return valve were on the market which comprised, in a pre-chamber situated towards the milk collector and joined to the valve body, a flap freely movable through this pre-chamber. Thus, the pre-chamber was only closed by this flap against the milk collector, this flap being held by tabs of the chamber wall bend inwardly and forming the connecting device when some peripheral openings were freed. However, such a construction is difficult to clean and, therefore, did not meet the hygienic requirements. Moreover, the flap was practically not guided centrally within the chamber so that it was enabled to take an inclined position whereupon proper operation was not ensured.

Now, breast pumps of the kind described at the outset have become known from U.S. Pat. No. 4,929,229, for example. There was an simple plug connection for the flap in the middle of the front surface of the valve provided in them, thus being easy to be detached and cleaned. A problem lies in that, although the milk is sucked off in the biological rhythm of a sucking baby, very different quantities of milk result from it which have to be conveyed to the milk collector, in most cases in the form of a connected receptacle. In the past, this resulted in various drawbacks in operation of such a breast pump. Namely, with a large quantity of milk, the milk could reach the pump unit which could easily be destroyed or at least was not usable for a long time up to repair or dismantling and cleaning.

Investigations of the applicant have shown that the aforementioned problem had various reasons which acted even the kind mentioned at the outset in such a way that damaging or soiling the pump unit is no longer possible. According to the invention, this is achieved by any of the characterizing clauses of claims 1, 8 or 15 and/or 20.

First of all, it has been recognized that, although the valve according to U.S. Pat. No. 4,929,229 solved the hygienic problem, it permitted only a reduced elasticity to the flap due to its central connection device. Certainly, there was some prejudice of those in the art that uniform closure of the plurality of throughput openings provided in the prior art could be achieved by a central connecting device. However, this prejudice turned out to be unfounded according to the investigations of the applicant. On the contrary, by providing a flap being hinged at the edge of the front surface, i.e. eccentrically, it is endowed with an increased flexibility. For it has been found that with a central arrangement of the connecting device, the flap has only the free radius along which it can exhibit its flexibility. In this way, the flap became, however, somewhat stiff, thus forming a not inconsiderable flow resistance even with the throughput opening being freed. By the construction according to the invention, in contrast, the freely flexible length of the flap is increased, and the flap obtains properties of a greater suppleness and elasticity so that it engages tightly the respective throughput opening under the action of suction, but frees under load the throughput opening practically without any resistance even with a small quantity of milk.

In order to solve the problem of the connection to the valve body, it would be possible, in fact, to provide a plug, analogously to the prior art, about within the region of the hinge which could be plugged into a plug opening on the front surface of the valve body. However, in accordance with exemplary embodiments of the present invention, cleaning is easily effected by detaching the fastening flange from the valve body, while, at the same time, the connecting device cannot have any detrimental effect to the hinge.

Just in the case where the flap has an enhanced elasticity and suppleness, in correspondence with the cited embodiment according to the invention, a single throughput opening cannot be made with any dimension, because the supple flap could jam in it during the suction stroke of the pumping unit. Therefore, an embodiment according to the present invention is particularly advantageous, because in this way a large throughput cross-section is ensured without the necessity to make an individual throughput opening too large.

A central connection was provided in the prior art not least because one feared too great an elasticity which could interfere with a proper closure of the respective throughput opening during the suction stroke of the pump unit. By an embodiment according to the invention the finite thickness of the margin surrounding closely the flap effects, in this way, sealing between it and the flap which is quickly sucked into the opening of the margin thus created during the suction stroke. The margin may, in this case, be thickened around the flap, but this is, in general, not necessary.

Certainly, the hinge could be constructed in a variety of ways. However, by an embodiment according to the invention a smooth, and therefore easily to clean, plastic hinge is obtained which can be easily produced integrally with the flap.

In the U.S. Pat. No. 4,929,229, and not only in it, the first branch channel runs about as a prolongation of the discharge channel, i.e. obliquely downwards. Therefore, a partition wall was inserted to inhibit any direct connection of the two channels. In practice, however, this was not very effective, because when milk dammed up at the valve it could reach the branch channel anyway and could not be removed from it. In accordance with an exemplary embodiment however, milk drains automatically even then without reaching the pump unit, if the quantity of milk should be as large that the valve is unable to let it through in a short time.

Within the scope of an exemplary embodiment of the invention it is sufficient, as such, if only some section of the first branch channel is upward directed, but it is preferred, in accordance with a further exemplary embodiment of the invention, that drainage into the milk collector can be achieved without any additional measure.

For it has been found that part of the problem is created by an inappropriate suction effect of the pump unit itself. However, by the measures according to an exemplary embodiment of the present invention one gains control not only of the problem of too large quantities of milk, but an additional effect of an, in case, more gentle suction less uncomfortable for the user will be obtained especially when also the features of alternate embodiments are provided which enable adaptation of the effective suction power to the user.

BRIEF DESCRIPTION OF THE DRAWING

Further details, features and advantages of the invention will become apparent from the following description of a preferred embodiment schematically illustrated in the drawing in which FIG. 1 shows a longitudinal section of a breast body, channel system and valve of a breast pump according to the invention, whereas FIG. 2 illustrates the valve according to the invention in a perspective view;

FIG. 3 is a view of a detail of FIG. 1 on a larger scale for illustrating a closure system according to the invention in its closed position for adjusting the supply of by-passing air, which is in FIG. 4 in partially opened position, whereas FIG. 5 represents the lid and the hub portion of this system in a perspective view.

DETAILED DESCRIPTION OF THE INVENTION

Figure 3:
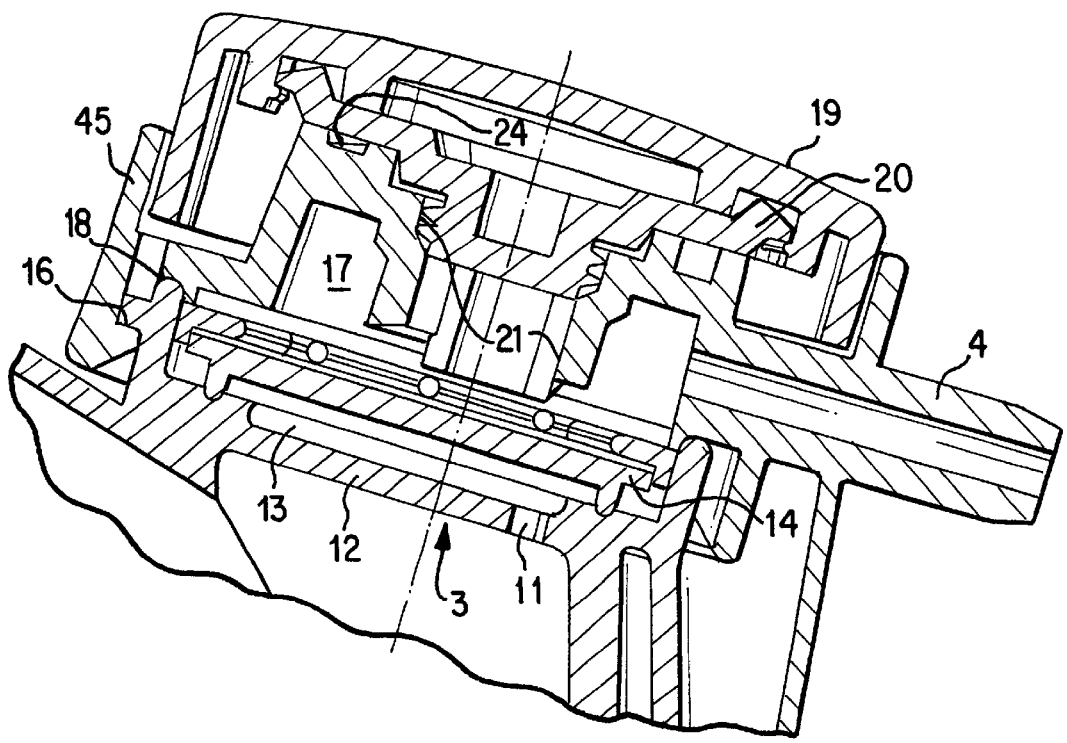

FIG. 1 shows a longitudinal cross-section of the upper part of a breast pump which includes a breast body 1 receiving the breast of a woman. Connected to the breast body 1 is a draining channel 2 being downwards inclined so that draining of milk pumped off is facilitated. This draining channel 2 branches at a branching point P. A first branch channel 3 is directed upwards and leads via a first connection socket 4 forming an angle with it to a pump unit 10 merely schematically indicated and known per se. A branch channel 5 leading downwards opens into a valve body 6 detachably mounted on it which is surrounded by a masking ring 7. Below the valve 6, a milk collector receptacle 8 is provided which can be connected to the upper part of the breast pump by means of a thread 9.

Even if a large quantity of milk were sucked off so that the throughput capacity of the valve body 6 were not be sufficient to drain this quantity quickly into the milk collector 8 (which could likewise be formed in another way), the level of the milk would first rise up to the level of the draining channel 2 where an enlarged volume with respect to the branch channel 5 for receiving the quantity of milk is at disposal. Thus, such milk could hardly reach the upward directed branch channel 3 and the pump unit 10 connected through the socket.

For the sake of safety, however, the upwards directed branch channel 3, 4 comprises also a flow resistance after the point P of the orifice of the first branch channel section 3 into the draining channel 2 in the direction towards the pump unit 10 which is, first of all, formed by a narrowing through opening 11 of reduced diameter in a transverse wall 12. It will be understood that such a flow resistance could be formed at any place along the line leading to the pump unit 10, but that application in the upwards directed branch channel section 3 is preferred.

After the through opening 11, when seen in the direction towards the pump unit 10, there is a small pre-chamber 13 which is covered by a further flow resistance in the form of a filter 14. This filter 14 consists suitably of a textile material, as has become known for rain coats, to permit penetration of air, but closing its pores in the case of rain under the influence of wetness. In the present case, the material is used not to impede by itself the suction effect of the pump unit 10, but to form an impermeable barrier in the case of milk passing into the pre-chamber 13 quite unlikely due to the measures already described.

In order to allow replacement of the filter 14, a socket 15 joining the first branch channel 3, and particularly being detachable, is provided which is attached to the branch channel 3 by means of a bayonet catch 16. Moreover, there is a further chamber 17 after the filter 14 which communicates with the relative thin connection socket 4 so that even with a failure of the filter 14, or when the filter is not inserted, there is enough space 13, 17 for possibly penetrated milk. A positioning element 18 holds the filter 14 in place so that it cannot bulge under suction effect.

A further measure for preventing intrusion of milk into the pump unit 10 consists in that the effective suction power of the pump unit acting upon the draining channel 2 and the breast body 1 is limited by the possibility of supplying by-padded air. As is apparent especially from FIG. 3, the socket 15 is closed by a lid 19 to this end which is connected to a hub portion 20. The hub portion 20 is seated in a central bearing 21 which is formed either integrally with or as a part separated from the socket 15. Suitably, there is a resilient connection piece 20a for establishing a firm connection with the socket 15. In this manner, the lid 19 is rotatably mounted to the socket 15 via the hub portion 20. FIG. 5 illustrates a positive connection between the lid 19 and the hub portion 20 which could be formed in any way, but in the simple embodiment represented is formed in such a manner that at least one projection (pin 34) extending parallely to the rotational axis, and one cogging recess (hole 35) engage each other.

Figure 4:
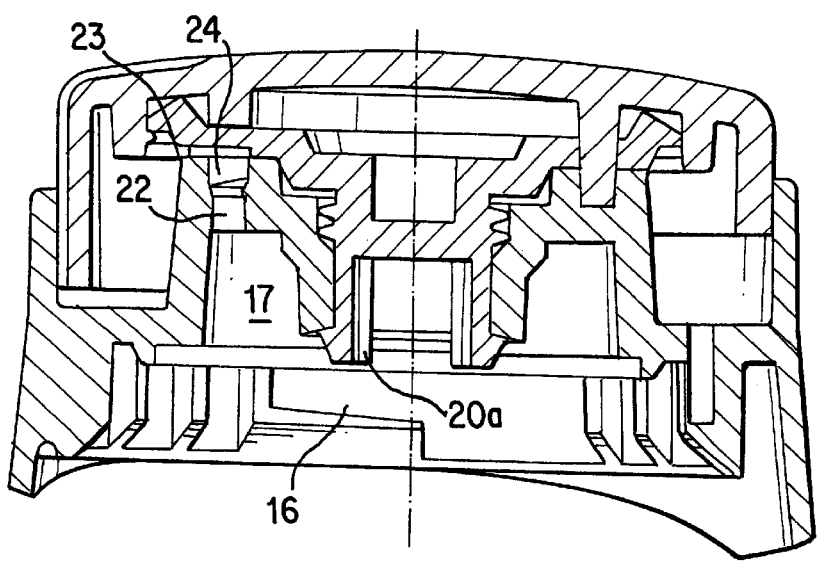

The socket 15 has a central cylinder ring 24 of a depth varying over its circumference and comprising an opening 22, which leads to the chamber 17 and which can be made more or less congruent with a by-padding air opening 23 (FIG. 4) of the socket 15. FIG. 5 shows the opening 23 which, in this embodiment, is channel-like, which, however, could extend alternatively in a wedge-shaped manner along a dotted line to vary its cross-section.

In this way, the effective suction power of the pump unit 10 is preferably adjustable either by closing the by-padding air opening 23 or by opening it more or less. It will be understood that this adjustment aid needs not to be provided in any case, because a by-padding air opening of unchangeable cross-section could, optionally, be closed manually similarly to the holes of a recorder. Moreover, the by-padding air opening 23 could be provided at any place within the line leading from the connection channel 2 to the pump unit 10, but an arrangement behind the flow resistance 11, 14 is particularly suitable, as will be well understood.

As may be seen especially from FIG. 2, the valve body 6 is provided with a plurality of throughput openings 26 for the breast milk at its front surface 25. This ensures a relative large throughput cross-section for the milk without the necessity to make an individual opening 26 too large. Although this measure is known per se, this was heretofore for other reasons. In the present case, it is connected to the special construction of the nonreturn flap 27 which may be connected to the valve body only over a hinge 28 situated at the margin of the front surface 25 as well as over a joining annular flange 29. As may be seen, the flap 27 together with the hinge is of pliable material, integrally formed in the manner of a plastic hinge so that a flat configuration is obtained easy to be cleaned after detaching.

By this eccentric pivot of the valve flap 27, a relative large free bending area is obtained which extends over the whole diameter of the flap 27 upon which a relative large twisting moment acts under the load of milk entering the valve body 6 so that such a flap can easily bend to free the openings 26 entirely. This is promoted, in addition, in that the large bending length of the flap 27 gives it a special suppleness. It is clear that the diameter of the flap 27 has to extend about as far that the outer diameter of the array of openings 26 is covered. Alternatively, supply of by-padding air could be attained by leaving an area of the radially outer openings 26 free, although this is not preferred for the reasons indicated above.

A peripheral margin 30 forming the hinge 28 is connected to the annular flange 29 and has a finite thickness in axial direction of the valve body 6. In this way, the flap 27 in closed position shown in FIG. 2 is closely surrounded by the margin 30. When the flap is open bending itself about the hinge 28, suction performed by the pump unit 10 acts first of all upon the portion of the flap 27 which is near the hinge 28 and the margin 30 and is increasingly sucked into the ring 30 from this side on, until it covers eventually the throughput openings completely.

In order to be able to clean the flap 27, it is pushed onto the valve body 6 by means of the annular flange 29. The valve body 6 has projections 31 into which the annular flange snaps in elastically for fastening. Instead of one row of projections 31, several rows could also be provided, but this is not particularly desirable in order to facilitate cleaning of the valve body 6 detachable from the branch channel 5. FIG. 2 shows also that the valve body may be provided with longitudinal ribs 32, but this is not necessary in all cases, and a substantially cylindrical shape is preferred, although other cross-sectional shapes are conceivable. Furthermore, it will be clear that instead of ribs 31 at the valve body 6, or in addition, an annular rib 33 may be provided at the free end of the annular flange 29 which locks then in an indentation of the valve body 6, e.g. behind the ribs 31.

Within the scope of the invention, it will be understood that each of the above-mentioned measures for preventing intrusion of milk into the pump unit 10 is of inventive significance, although its realization in common ensures a maximum of safety.

It will be appreciated by those skilled in the art that the present invention can be embodied in other specific forms without departing from the spirit or essential characteristics thereof. The presently disclosed embodiments are therefore considered in all respects to be illustrative and not restricted. The scope of the invention is indicated by the appended claims rather than the foregoing description and all changes that come within the meaning and range and equivalence thereof are intended to be embraced therein.

What is claimed is:

1. Breast pump comprising:
   a breast body for receiving the breast of a woman and having a draining channel and a pump unit branching from it through a first branch channel; and
   a further branch channel leading over a nonreturn valve to a milk collector, said valve being provided with a valve body including at least one throughput opening in a front surface for breast milk pumped off and a flap of pliable material closing this opening upon sucking off, said flap being removably connected to the valve body via a connection device, the connection device including a hinge situated at a margin of the front surface for a flap which extends freely from this hinge over at least part of the front surface;
   wherein the connection device comprises a fastening flange at least partially surrounding the valve body and a peripheral margin extending radially inward from the fastening flange and forming the hinge wherein the peripheral margin closely surrounds the flap in a closed position covering the throughput opening.

2. Breast pump according to claim 1, wherein the fastening flange as well as the valve body are substantially cylindrical.

3. Breast pump according to claim 2, wherein the least one of the fastening flange and the valve body comprise at least one of a projection and at least one indentation for interengaging connection.

4. Breast pump according to claim 1, wherein the flap, which extends freely from the hinge over the front surface, covers a plurality of throughput openings.

5. Breast pump according to claim 1, wherein the flap together with the connection device including the hinge are made of plastic material.

* * * * *